(12) United States Patent
Balasubramaniam

(10) Patent No.: US 12,303,356 B2
(45) Date of Patent: May 20, 2025

(54) APPARATUSES AND METHODS FOR IMPROVING POST-OPERATIVE RECOVERY FROM SURGERY

(71) Applicant: Noleus Technologies, Inc., Sugar Land, TX (US)

(72) Inventor: Swarna Balasubramaniam, Sugar Land, TX (US)

(73) Assignee: Noleus Technologies, Inc., Sugar Land, TX (US)

( * ) Notice: Subject to any disclaimer, the term of this patent is extended or adjusted under 35 U.S.C. 154(b) by 617 days.

(21) Appl. No.: 17/177,601

(22) Filed: Feb. 17, 2021

(65) Prior Publication Data

US 2021/0228787 A1 Jul. 29, 2021

Related U.S. Application Data

(62) Division of application No. 15/221,509, filed on Jul. 27, 2016, now Pat. No. 10,960,113.

(Continued)

(51) Int. Cl.
*A61F 13/01* (2024.01)
*A61F 13/00* (2024.01)
(Continued)

(52) U.S. Cl.
CPC .. *A61F 13/01017* (2024.01); *A61F 13/01029* (2024.01); *A61F 13/05* (2024.01);
(Continued)

(58) Field of Classification Search
CPC .......... A61M 35/00; A61M 1/00; A61M 3/00; A61M 31/00; A61M 1/916; A61M 1/915; A61M 1/92; A61M 2210/1021; A61M 2210/1042; A61F 13/00; A61F 13/02; A61F 8/44; A61F 13/00017; A61F 13/00029; A61F 13/00068; A61F 2013/00093;

(Continued)

(56) References Cited

U.S. PATENT DOCUMENTS 2,896,618 A 7/1959 Schaefer
5,985,395 A 11/1999 Comstock et al.
(Continued)

FOREIGN PATENT DOCUMENTS

WO WO 2014/4165275 10/2014
WO WO 2017/019810 2/2017

OTHER PUBLICATIONS

Farlex Partner Medical Dictionary © (Year: 2012).*

(Continued)

*Primary Examiner* — Andrew J Mensh
(74) *Attorney, Agent, or Firm* — Julian D. Forman

(57) ABSTRACT

This disclosure relates to apparatuses and methods for preventing the onset and progression of POI. In one example, a fan-like polyurethane heat-sealed bilayer that surrounds a plurality of wedge-shaped foam strips that join at a collecting foam portion, is subjected to negative pressure provided through silicone tubing which is sealed to the perforated collecting foam portion. Such negative pressure applied for approximately 48 to 72 hours after closure of the abdomen, helps prevent POI which in turn enhances patient recovery, and reduces the length of their hospital stay.

19 Claims, 10 Drawing Sheets

Related U.S. Application Data

(60) Provisional application No. 62/197,552, filed on Jul. 27, 2015.

(51) Int. Cl.
*A61F 13/05* (2024.01)
*A61L 26/00* (2006.01)
*A61M 1/00* (2006.01)

(52) U.S. Cl.
CPC ....... *A61L 26/0014* (2013.01); *A61L 26/0019* (2013.01); *A61M 1/916* (2021.05); *A61F 2013/00093* (2013.01); *A61F 2013/0028* (2013.01); *A61M 1/915* (2021.05); *A61M 1/92* (2021.05); *A61M 2210/1021* (2013.01); *A61M 2210/1042* (2013.01)

(58) Field of Classification Search
CPC ........ A61F 2013/0028; A61F 13/01017; A61F 13/05; A61F 13/01029; A61L 26/0014; A61L 26/0019
USPC .......................................................... 604/319
See application file for complete search history.

(56) References Cited

U.S. PATENT DOCUMENTS

| | | | |
|---|---|---|---|
| 7,988,680 | B2 | 8/2011 | Lockwood et al. |
| 8,148,596 | B2 | 4/2012 | Miau et al. |
| 8,216,175 | B2 | 7/2012 | Hutchinson et al. |
| 8,672,903 | B2 | 3/2014 | Hunt et al. |
| 8,791,315 | B2 | 7/2014 | Lattimore et al. |
| 8,926,574 | B2 | 1/2015 | Croizat et al. |
| 8,974,428 | B2 | 3/2015 | Freedman et al. |
| 9,302,034 | B2 | 4/2016 | Corley |
| 10,960,113 | B2 | 3/2021 | Balasubramaniam |
| 2005/0131327 | A1 | 6/2005 | Lockwood et al. |
| 2005/0143697 | A1 | 6/2005 | Riesinger |
| 2011/0087178 | A2 | 4/2011 | Weston |
| 2012/0116334 | A1 | 5/2012 | Albert et al. |
| 2012/0136326 | A1* | 5/2012 | Croizat ............. A61F 13/00987 604/319 |
| 2013/0245527 | A1 | 9/2013 | Croizat et al. |
| 2014/0039468 | A1* | 2/2014 | Dunn .................... A61M 1/71 604/319 |
| 2014/0068914 | A1 | 3/2014 | Coward et al. |
| 2014/0094761 | A1 | 4/2014 | Corley |
| 2014/0221947 | A1 | 8/2014 | Hunt et al. |
| 2015/0080788 | A1* | 3/2015 | Blott ...................... A61M 1/94 604/30 |
| 2017/0049943 | A1 | 2/2017 | Balasubramaniam |
| 2018/0333522 | A1* | 11/2018 | Pratt .................... A61F 13/148 |

OTHER PUBLICATIONS

American Heritage® Dictionary of the English Language (Year: 2016).*

Gabriel, Negative Pressure Wound Therapy with Instillation: A Pilot Study Describing a New Method for Treating nfected Wounds. International Wound Journal. 2008. vol. 5; No. 3; p. 401; col. 1; paragraph 2.

Holte et al. Pathophysiology and Clinical Implications of Perioperative Fluid Excess, British Journal of Anaesthesia, 2002,89: pp. 622-632.

Huang, C., Effect of Negative Pressure Wound Therapy onWound Healing, pp. 301-331, Journal: Current Problem in Surgery 51, 2014, www.elsevier.com/locate/cpsurg.

Lobo et al. Effect of salt and water balance on recovery of gastrointestinal function after elective colonic resection: a andomised controlled trial, The Lancet, vol. 359, May 25, 2002, pp. 1812-1818.

NICE {National Institute for Health and Care Excellence), Vacuum {negative pressure) therapyfor open abdominal , vounds, Nov. 2013, pp. 4, http://publications.nice.org.uk/ifp467.

Uray et al., Edema-Induced Intestinal Dysfunction is Mediated by Stat3 Activation; SHOCK, 2007, vol. 28, No. 2, pp. 39-244.

Vather et al. Proceedings of the Australian Physiological Society Symposium: Advances in Methods for Intestinal Motility, Clinical and Experimental Pharmacology and Physiology, 2014, 41, pp. 358-370.

Vaughan-Shaw et al. Oedema is associated with clinical outcome following emergency abdominal surgery, Ann R Coll Surg Engl 2013; 95: pp. 390-396.

* cited by examiner

APPARATUSES AND METHODS FOR IMPROVING POST-OPERATIVE RECOVERY FROM SURGERY

CROSS-REFERENCE TO RELATED APPLICATION

This application is a divisional of U.S. patent application Ser. No. 15/221,509 filed Jul. 27, 2016, which claims the benefit of the filing date of U.S. Provisional Patent Application No. 62/197,552, filed on Jul. 27, 2015, by the inventor of this application, and incorporated herein by reference.

TECHNICAL FIELD OF THE INVENTION

The present disclosure relates generally to apparatuses and methods for improving post-operative recovery from bowel surgery. More particularly, the disclosure relates to apparatuses and methods for preventing the onset and progression of Postoperative Ileus.

BACKGROUND

Postoperative Ileus (POI) is a transient impairment of bowel motility often resulting after abdominal surgery. POI is a common cause in delaying the body's return to normal gastrointestinal ("GI") function. Despite significant research investigating how to reduce this multi-factorial phenomenon, a single strategy has not been shown to reduce POI's significant effects on length of stay (LOS) and hospital costs. POI is often responsible for extended hospital stays because hospitals will not discharge a patient until after a bowel movement. POI may also be responsible for some post-surgical readmissions to the hospital. As noted by others, the duration of the resulting hospital stay varies with the anatomic location of the surgery, the degree of surgical manipulation, and the magnitude of inflammatory responses. When the surgery directly affects the GI track, the resulting POI is often more severe and takes longer to correct. Traditional treatment of POI includes mobilization, administration of laxatives, open abdomen surgical techniques, and prokinetic agents. Accordingly, there is a need for alternative approaches for treating POI.

SUMMARY

In view of the aforementioned problems and trends, embodiments of the present disclosure provide apparatuses and methods for preventing and treating POI.

According to a first aspect of the disclosure, an apparatus includes a bilayer encompassing a plurality of foam strips.

In another aspect of the disclosure, a method for preventing the onset and progression of POI includes the steps of placing a plurality of foam strips enveloped in a bilayer on the bowels; and applying negative vacuum pressure therapy to the plurality of strips.

In yet another aspect of the disclosure, an apparatus for decreasing post-operative infections or hematoma includes a bilayer drape for removing blood and fluid in the post-operative abdominal cavity, wherein the drape is fluidly connected to a negative pressure delivery means.

Other aspects of the embodiments described herein will become apparent from the following description and the accompanying drawings, illustrating the principles of the embodiments by way of example only.

BRIEF DESCRIPTION OF THE DRAWINGS

The following figures form part of the present specification and are included to further demonstrate certain aspects of the present claimed subject matter, and should not be used to limit or define the present claimed subject matter. The present claimed subject matter may be better understood by reference to one or more of these drawings in combination with the description of embodiments presented herein. Consequently, a more complete understanding of the present embodiments and further features and advantages thereof may be acquired by referring to the following description taken in conjunction with the accompanying drawings, in which like reference numerals may identify like elements, wherein:

NOTATION AND NOMENCLATURE

Figure 1:
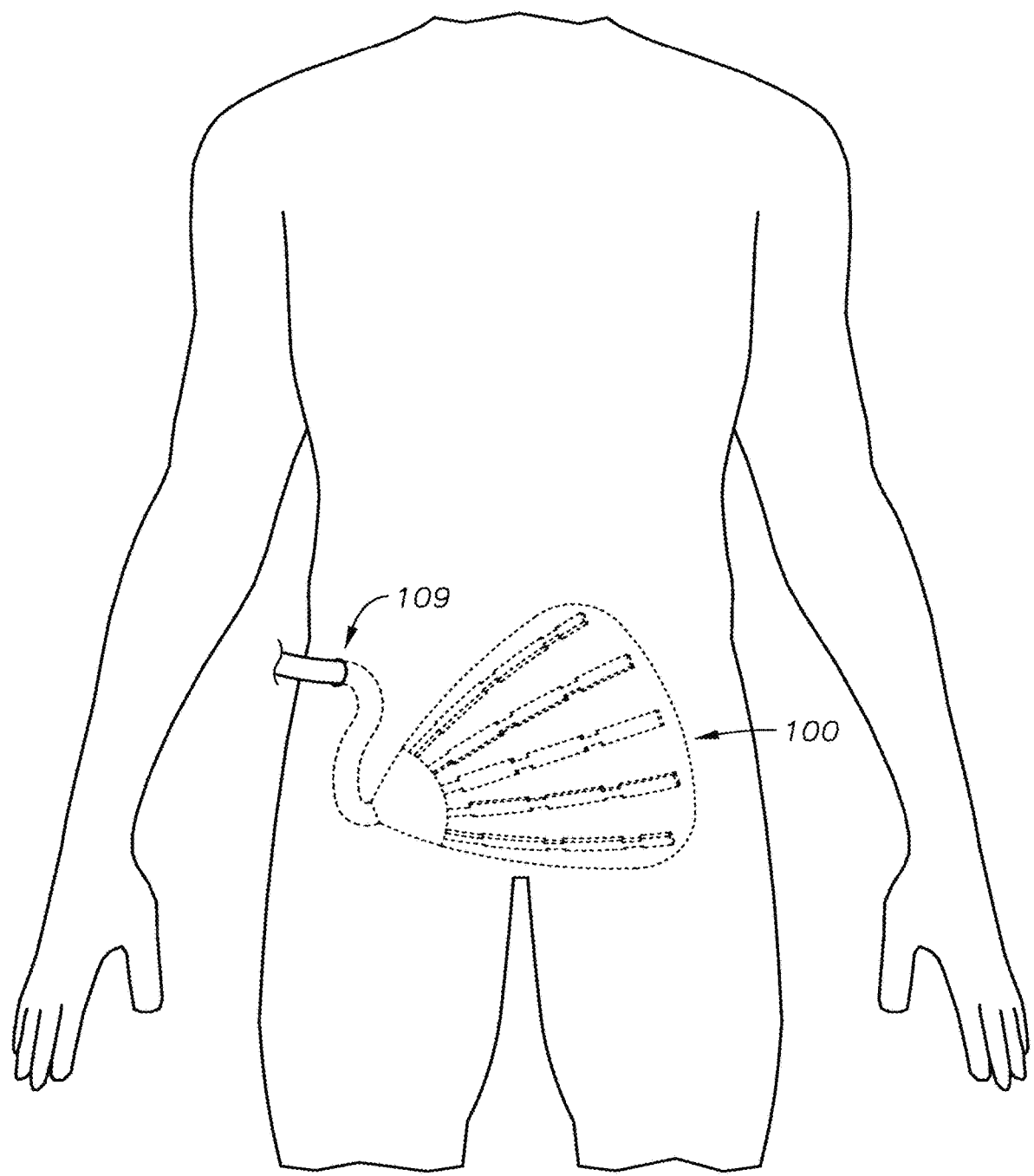
FIG. 1 is a perspective of an embodiment wherein the apparatus is in situ inside a human.

Certain terms are used throughout the following description and claims to refer to particular system components and configurations. As one skilled in the art will appreciate, the same component may be referred to by different names. This document does not intend to distinguish between components that differ in name but not function. In the following discussion and in the claims, the terms "including" and "comprising" are used in an open-ended fashion, and thus should be interpreted to mean "including, but not limited to . . . "

The term "patient" is used throughout the specification to describe an animal, human or non-human, to whom treatment according to the methods of the present disclosure is provided. Veterinary applications are clearly anticipated by the present disclosure. The term includes but is not limited to mammals, e.g., humans, other primates, pigs, rodents such as mice and rats, rabbits, guinea pigs, hamsters, cows, horses, cats, dogs, sheep and goats. The term "treat (ment)," is used herein to describe delaying the onset of, inhibiting, preventing, or alleviating the effects of a condition, e.g., ileus. The term "donor" or "donor patient" as used herein refers to a patient (human or non-human) from whom an organ or tissue can be obtained for the purposes of transplantation to a recipient patient. The term "recipient" or "recipient patient" refers to a patient (human or non-human) into which an organ or tissue can be transferred.

The term "ileus" as used herein generally refers to partial or complete paralysis or dysmotility of the gastrointestinal tract. Ileus can occur throughout the gastrointestinal tract, or can involve only one or several sections thereof, e.g., stomach, small intestine, or colon. The skilled practitioner will appreciate that ileus can be caused by a great number of factors that include, for example, surgery (e.g., any surgery involving laparotomy, e.g., small intestinal transplantation (SITx); or any surgery involving laparoscopy); intestinal ischaemia; retroperitoneal hematoma; intraabdominal sepsis; intraperitoneal inflammation; acute appendicitis; choecystitis; pancreatitis; ureteric colic; thoracic lesions; basal pneumonia; myocardial infarction; metabolic disturbances, e.g., those that result in decreased potassium levels; drugs, e.g., prolonged use of opiates; and traumas, e.g., fractures of the spine and rib fractures (see, e.g., Oxford Textbook of Surgery, Morris and Malt, Eds., Oxford University Press (1994)). The term also includes post-partum ileus, which is a common problem for women in the period following parturition, e.g., following vaginal delivery ("natural childbirth") or surgically-assisted parturition. As used herein, the term "post-operative ileus" or POI refers to ileus experienced by a patient following any surgical procedure, e.g., abdominal surgery.

DETAILED DESCRIPTION

The foregoing description of the figures is provided for the convenience of the reader. It should be understood, however, that the embodiments are not limited to the precise arrangements and configurations shown in the figures. Also, the figures are not necessarily drawn to scale, and certain features may be shown exaggerated in scale or in generalized or schematic form, in the interest of clarity and conciseness. The same or similar parts may be marked with the same or similar reference numerals.

While various embodiments are described herein, it should be appreciated that the present disclosure encompasses many inventive concepts that may be embodied in a wide variety of contexts. The following detailed description of exemplary embodiments, read in conjunction with the accompanying drawings, is merely illustrative and is not to be taken as limiting the scope of the invention, as it would be impossible or impractical to include all of the possible embodiments and contexts of the invention in this disclosure. Upon reading this disclosure, many alternative embodiments of the present invention will be apparent to persons of ordinary skill in the art. The scope of the invention is defined by the appended claims and equivalents thereof.

Illustrative embodiments of the invention are described below. In the interest of clarity, not all features of an actual implementation are described in this specification. In the development of any such actual embodiment, numerous implementation-specific decisions may need to be made to achieve the design-specific goals, which may vary from one implementation to another. It will be appreciated that such a development effort, while possibly complex and time-consuming, would nevertheless be a routine undertaking for persons of ordinary skill in the art having the benefit of this disclosure.

The return of normal bowel function following any type of surgery is usually a predictable event. The return of the small intestine's peristaltic action begins first, usually 4 to 8 hours post-operatively, and generally becomes complete around 24 hours. The colon resumes its function between 48 and 72 hours postoperatively. However, in some cases, there is a delay or permanent failure of normal bowel function leading to ileus. The pathogenesis of POI is poorly understood, but multiple causes have been suggested: sympathetic reflexes; inhibitory humoral agents; release of norepinephrine from the bowel wall; and the effects of anesthesia agents, opiates, and inflammation.

The surgery can be any surgery that causes and/or puts the patient at risk for ileus. For example, the surgery can involve manipulation (e.g., touching (directly or indirectly)) of the gastrointestinal tract, e.g., the stomach and/or intestines, e.g., small or large intestine (e.g., the colon), and can be a surgery involving laparotomy or not involving laparotomy (e.g., surgeries involving laparoscopy). In certain embodiments, the surgery can be transplant surgery or non-transplant surgery, e.g., surgery involving any organ(s) or tissue(s) in the abdomen, e.g., surgery of the urogenital system (e.g., kidneys, ureter, and/or bladder; and reproductive organs (e.g., uterus, ovaries, and/or fallopian tubes)); the digestive system (e.g., the stomach, small intestine, large intestine (e.g., the colon), appendix, gallbladder, liver, spleen, and/or pancreas); the lymphatic system; the respiratory system (e.g., the lungs); the diaphragm; surgery to treat cancer of any organ or tissue within the abdomen; endometrial surgery; and orthopedic surgeries, e.g., hip surgery.

The treatment of open or chronic wounds by means of applying negative pressure to the site of the wound, where the wound is too large to spontaneously close or otherwise fails to heal, is known in the art. Negative pressure wound treatment (NPWT) systems currently known commonly involve placing a cover that is impermeable to liquids over the wound, using various mechanisms to seal the cover to the tissue of the patient surrounding the wound, and connecting a source of negative pressure (such as a vacuum pump) to the cover whereby an area of negative pressure is created under the cover in the area of the wound.

NPWT promotes the healing of open wounds (such as those that arise during and after surgery) by applying a vacuum through a special sealed dressing. The continued vacuum draws out fluid from the wound and increases blood flow to the area. The vacuum may be applied continuously or intermittently, depending on the type of wound being treated and the clinical objectives. Typically, the dressing is changed several times. The dressings used for the technique include open-cell foam dressings and gauze, sealed with an occlusive dressing or polyurethane which may or may not be permeable, which is intended to contain the vacuum at the wound site. Under certain circumstances, it may be desirable or necessary for NPWT devices and systems to allow delivery of fluids, such as saline or antibiotics to irrigate the wound. The intermittent removal of used fluid supports the cleaning and drainage of the wound bed.

An injury or surgery to the abdomen can result in a wound that cannot be closed straight away. The wound may need to be left open to allow further treatment, or to allow infection to clear. The internal organs, including the bowel, may be left exposed. Sometimes fistulas can form (a fistula is an abnormal passage between either the inside of the body and the skin or 2 internal organs). Open abdomens may be managed in different ways, including using a "Bogota bag" (a sterile plastic bag to contain the bowel), systems with a zip, or dressings. The UK's National Institute for Health and Care Excellence (NICE) concluded that using vacuum therapy to manage open abdomen should be another recommended treatment option for government-provided health insurance such as the UK's National Health Service.

The 7 studies that NICE reviewed involved a total of 5263 patients. Generally, they showed that: Roughly half (45-58%) of patients' wounds could be surgically closed after vacuum therapy compared with rates of 13-78% for other types of temporary dressing. A small number of patients needed an artificial patch to the abdominal wall afterwards—but this also happened after other techniques were used. The proportion of patients who died after vacuum therapy (22-30%) was similar to the number who died after other types of temporary dressing (16-33%). Again, there was no evidence that the deaths were linked to the procedure used.

As already noted, the goals of vacuum therapy are to remove infected material, stop fluid from escaping and help a wound heal. A permeable film, which allows fluid to pass through it, is placed over the wound and a foam sponge or other dressing, discussed further below, such as gauze is placed on top. A drainage tube is placed in the sponge and everything is covered with a transparent sticky film to seal the wound. A small pump then sucks away excess fluid from the wound (the vacuum part of the treatment). A sensing device in the form of a pad placed on top of the foam may be used to make sure that the right amount of suction is used.

Another variant for NPWT is as follows: a dressing or filler material such as foam is fitted to the contours of a wound (which is first covered with a non-adherent dressing film) and the overlying foam is then sealed with a transparent film. A drainage tube is connected to the dressing through an opening of the transparent film. A vacuum tube is connected through an opening in the film drape to a canister on the side of a vacuum pump or vacuum source, turning an open wound into a controlled, closed wound while removing excess fluid from the wound bed to enhance circulation and remove wound fluids. This creates a moist healing environment and reduces edema. This technique is usually used with chronic wounds or wounds that are expected to present difficulties while healing (such as those associated with diabetes).

Such NPWT systems have been commercialized, for example, by Kinetic Concepts, Inc. of San Antonio, Tex., with its proprietary V.A.C.® product line. In practice, the application to a wound of negative gauge pressure, typically involves the mechanical-like contraction of the wound with simultaneous removal of excess fluid. In this manner, V.A.C.® therapy augments the body's natural inflammatory process while alleviating many of the known intrinsic side effects, such as the production of edema caused by increased blood flow absent the necessary vascular structure for proper venous return. As a result, V.A.C.® therapy has been shown to be highly successful in the promotion of wound closure, healing many wounds previously thought largely untreatable. However, treatment utilizing V.A.C.® therapy has been largely limited to open surface wounds. This procedure was approved for reimbursement by the Centers for Medicare and Medicaid Services in 2001.

The second generation system also developed by Kinetic Concepts, Inc. which is commonly used for open abdomen (OA) or laparotomy situations is similar in design to the V.A.C.® product line except for the visceral protective layer (VPL) that contains six foam extensions and provides for improved fluid removal. This ABThera™ OA NPT System uses a non-adherent fenestrated polyurethane, which separates the bowel from the abdominal wall and removes fluid using negative pressure. The ABThera™ Perforated Foam provides medial tension to help minimize fascial retraction and loss of domain. The ABThera™ Visceral Protective Layer provides separation between the abdominal wall and viscera, protecting abdominal contents, which in turn enhances fluid removal. There are no sutures required for placement, which allows for easy removal and replacement. This system has the advantage of faster, more efficient fluid removal as well as enhanced ease of use. However, because of the bulkiness of this system, the abdominal cavity must remain open for the duration of its use. When edema and swelling have been reduced sufficiently, the entire ABThera™ OA NPT System is removed and the abdominal cavity is closed. This may or may not correlate with the patient regaining full bowel function. Thus, there is no apparatus that is intended to prevent POI and help patients recover full bowel function after closure of the abdominal cavity.

The present disclosure teaches apparatuses and methods for improving post-operative recovery from bowel surgery. More particularly, the disclosure relates to apparatuses and methods for preventing the onset and progression of Post-operative Ileus. In one embodiment, as shown in FIG. 1, a fan-like polyurethane sealed (preferably with heat) bilayer that surrounds a plurality of wedge-shaped foam strips that join at a collecting foam portion, is subjected to negative pressure provided by silicone tubing which is connected to the collecting foam portion. Such negative pressure, applied for approximately 48 to 72 hours after closure of the abdomen, prevents POI, which in turn enhances patient recovery and reduces the length of their hospital stay.

Conventional skin/wound covering materials such as dressings are comprised of a bilayer or two layers of material (or film), each layer having specific properties. These conventional dressings for covering cuts, wounds, burns and the like, protect a patient's tissues during the healing process. One layer may include a tacky polymer complex layer for adhesively contacting the skin, which is sealed to a second water vapor-permeable backing layer. The polymer complex layer is produced by mixing together solutions of two hydrophilic polymers which are coprecipitatable, when mixed together, to form a water-insoluble complex. An example of a pair of such polymers is polyacrylic acid and polyethylene oxide.

A modified version of the conventional dressing is used for NPWT. The wound covering used for NPWT typically includes a core layer of a synthetic or semi-synthetic filling, sponge or foam material, such as a cotton gauze or a polyurethane (PU), polyethylene (PE) or polyvinyl alcohol (PVA) sponge which is sealed airtight between two thin polymer (also made of PU, PE or PVA) films, which form a bilayer around the sponge.

The dressing or foam/sponge strips used within the bilayer depends on the type of wound, clinical objectives and patient. For pain sensitive patients with shallow or irregular wounds, wounds with undermining or explored tracts or tunnels, gauze may be used. However, for the present disclosure, foam is preferred as it may be cut easily to fit a patient's abdominal space and performs better when aggressive granulation formation and wound contraction is the desired goal.

It should be apparent that while the present disclosure references two dimensional features, the apparatus is three dimensional. As such it is flexible and pliable and intended to be placed around the bowels so as to surround and encompass them within the abdominal cavity. For example, the non-tubing portion of the apparatus in FIG. 1 should be preferably placed at the inlet to the pelvis, almost horizontally or up to a 45 degree angle on the height axis of a supine patient, across the lower abdomen just at the level of the pubis in front and the sacral ala in the posterior.

The apparatus is meant to be a placed temporarily in the abdomen. It is initially placed on the pelvic floor and expanded and flattened over the bowels while the abdomen is open. Cushioned support for the bowels (similar to a hammock supporting a person), is also provided by the apparatus which may enhance patient recovery of bowel function. Placement of the apparatus should be to maximize contact with a large amount of bowel surface area so that negative pressure is applied to most of the surface area of the bowel. Maximizing the surface area interactions between negative pressure and the bowels promotes bowel healing (countering trauma that may arise during and after surgery). By applying a vacuum through a sealed foam bilayer as disclosed herein, the continued vacuum draws out fluid from the bowels and increases blood flow to the area.

As shown in FIG. 1, tubing from the apparatus extends to the outside of the patient's abdomen so that a negative pressure means can be attached. The abdomen is then closed using conventional surgical means known in the art. Once a patient exhibits restoration of bowel function and there is little likelihood of ileus, the apparatus is removed by gently tugging on the tubing portion and pulling it out. The presence of parallel pleats or indentations (element 108 in FIG. 2; not shown in FIG. 1) between the foam wedge-shaped strips facilitates retraction of the apparatus through the approximately 2 cm incision 109 on the patient's abdomen. The "approximately" 2 cm incision 109 may vary by ±10% or by a dimension conventionally used in the surgical art or required for conventional tubing to connect device 100 to any source of negative pressure.

For the present disclosure, none of the filler (foam or sponge strip) material is in direct contact with any viscera or tissue. However, teachings from the analogous art as they relate to filler materials used in conventional wound dressings (which may come into direct contact with viscera and/or tissue), with proven biocompatibility and safety can lead to optimization of the foam strip materials that are preferable for the present disclosure. Three types of filler material are used over a wound surface: open-cell foam, gauze and transparent film, or honeycombed textiles with a dimpled wound contact surface. In general, foam dressings are used to fill open cavity wounds and can be cut to size to fit wounds. The foam dressing is applied, filling the wound and then a film drape is applied over the top to create a seal around the dressing. Open weave cotton gauze can be covered with a transparent film, and a flat drain is sandwiched in gauze and placed onto the wound. The film drape covers the wound and creates a complete seal, and then the drain is connected to the pump via the tubing. It is contemplated that the filler material of the present disclosure includes preferably open cell foam encased in a polyethylene bilayer. However, a single conventional filler material (e.g. only open cell foam) or a combination of other filler materials may be used. It should be noted that the term foam and sponge are used interchangeably.

Companies such as UFP Technologies focus on designing and fabricating dynamic dressings for NPWT that promote and enhance healing as well as expedite the healing process for a patient. Foam is the most commonly used dressing in negative pressure wound therapy because it is easy to apply, suitable for a diverse range of wound types and sizes, and can effectively achieve the goals of NPWT, including a reduction in wound dimensions and improvement in granulation tissue of the wound bed. More specifically, reticulated polyurethane medical foams are preferred as they are easy to clean, impervious to microbial organisms, and can be made with fungicidal and bactericidal additives for added safety. With open-cell, hydrophobic properties, reticulated foams help evenly distribute negative pressure at the wound site. The pore size of the reticulated foam appears to be a large determinant on the rate of granulation tissue formation. Thus, according to embodiments of the present disclosure, pore size throughout the foam/sponge strips may be manipulated (varied) depending on the particular application. The pore sizes in the reticulated foam also known as open cell foams may be varied depending on the application requirements. These reticulated foams may also be further perforated to generate larger pores (or slits or perforations) which facilitate fluid communication between bowel tissue, each layer of the bilayer, the foam strips and pressure from the negative pressure means.

As noted in a recent review article by C. Huang et al., the commercial KCI VAC system, uses three general types of foam: black polyurethane ether (V.A.C. GranuFoam, KCI), black polyurethane ester (V.A.C. VeraFlow, KCI), and white polyvinyl alcohol (V.A.C. WhiteFoam, KCI). The traditional polyurethane ether foam is hydrophobic, whereas the polyvinyl alcohol and polyurethane ester foams are more hydrophilic. The polyurethane ester devices are designed for use with instillation therapy. The properties of the traditional polyurethane ether foams are preferred for wounds with large fluid drainage and for stimulating granulation tissue formation as needed for OA situations. In contrast, the polyvinyl alcohol sponges have been used in cases where the wound tunnels or when delicate underlying structures, such as tendons or blood vessels, need to be protected. Finally, the increased density and smaller pores of the white polyvinyl alcohol based foam helps to restrict ingrowth of granulation tissue, thereby diminishing pain associated with dressing changes and reducing risk when hypergranulation is a concern. Additionally, the foam may be permeated with silver, which provides an effective barrier to bacterial penetration while offering advanced moist wound healing technologies.

Furthermore, in a preferred embodiment the reticulated polyurethane foam is combined with thermoplastic polyurethane (TPU) films which form the previously described bilayer encasing the foam. TPU films are used widely for medical applications because they offer excellent water, fungus and abrasion resistance. They are also soft, breathable, and conformable which help to enhance patient comfort. These semi-transparent TPU films are non-adherent to human tissue, making replacement and removal painless for patients. For example, manufacturers such as Lubrizol Advanced Materials, Inc. (Cleveland, OH) produces a variety of TPU films that are strong, flexible, impermeable, biostable and solvent resistant. Thermoplastics, rather than thermoset films are preferred as they remain pliable which facilitates placement and removal from the abdominal cavity. Pliability is also important as it facilitates maximization of surface areas interactions between the apparatus provided negative pressure and the bowels.

Alternatively, products such as Acticoat® produced by Smith & Nephew, Inc. (Mississauga, Ontario, Canada) may be used for the encapsulated reticulated foam portion of the apparatus. In particular, a rayon/polyester inner dressing core which helps manage moisture level is enveloped in a silver-coated high-density polyethylene mesh bilayer which facilitates the passage of silver through the dressing. The nanocrystalline coating of pure silver delivers antimicrobial barrier activity within 30 minutes-faster than other forms of silver. Acticoat®'s antimicrobial technology is able to produce silver-coated polyethylene films that can release an effective concentration of silver over several days. Thus, as silver ions are consumed, additional silver is released from the dressing to provide an effective antimicrobial barrier. Such silver-based dressing technology delivers fast-acting, long-lasting antimicrobial barrier control which may assist in preventing contamination of the surrounding tissue. Furthermore, this feature may reduce infections contracted during hospitalization caused by "superbugs" such as MRSA. The sustained release of silver also means fewer dressing changes, resulting in less exposure of the tissue bed to the environment. This reduces the risk of infection, further lowering costs to hospitals.

In a preferred embodiment, the bilayer is comprised of a medical grade TPU with each bilayer being from approximately 160 to 800 microns in thickness. The fully extended fan-like apparatus may have a radius of approximately 30 cm to provide approximately 1,413 cm² of surface area, the reticulated encapsulated foam thickness is 10 mm while each polyurethane bilayer has a thickness of 160 microns. The shelf life is approximately 3 years at room temperature and all components are sterile and latex free. The preferred storage temperature range is −20° F. (−29° C.) to 140° F. (60° C.). The preferred operating temperature range is 50° F. (10° C.) to 100° F. (38° C.) and the altitude range for optimum performance is 0 to 8,000 ft (0 to 2438 m). The dimensions of the contracted or compressed device should be less than 2 cm so that the necessary abdominal incision for retracting the apparatus is similarly a maximum of 2 cm.

The apparatus may be of any shape (circular, square, trapezoid etc.) but for optimal performance should be semi-circular or pie slice-shaped or fan-like when fully extended. Preferably, there are very few right angles on the apparatus; a configuration with few or no right angles mitigates difficulties in retraction and removal of the apparatus from a patient's abdomen. Thus, all edges (perimeter) of the apparatus are preferably rounded and sealed. The preferred means for sealing is the application of heat to the bilayer as this is simple (does not require the application of any additional attachment means) and safe (chemicals attachment such as with glues might harm patients). However, other means of sealing and attachment known in the art are contemplated by this disclosure. Depending on the size of the abdominal cavity and level of fatty tissue present, it may be necessary to place more than one of the apparatus within the abdomen of a patient, to fully encompass their bowels. In contrast, should the patient have a smaller frame with smaller viscera, the apparatus may be cut to reduce the radius (or size) to accommodate smaller abdominal cavities.

Figure 2:
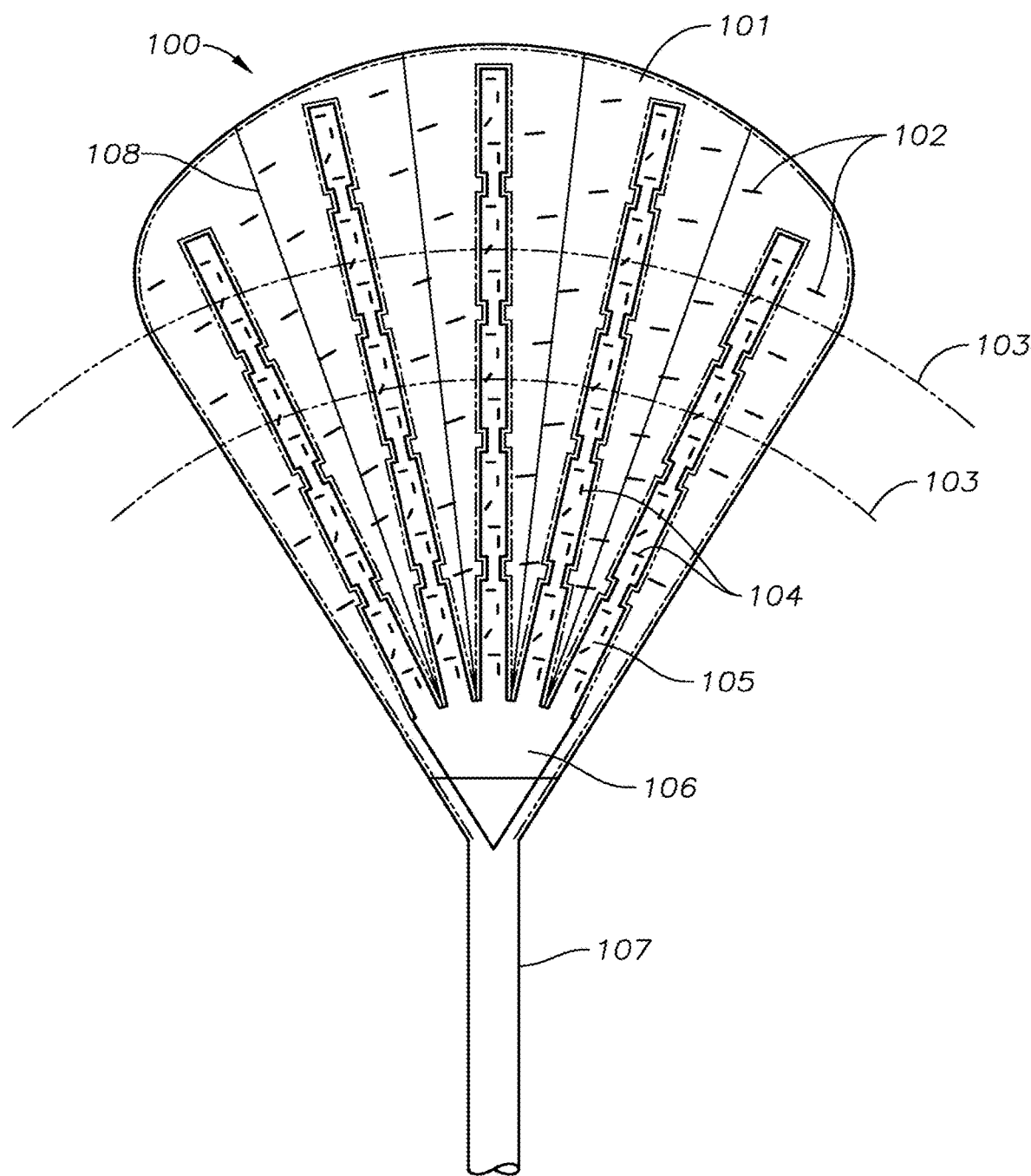
FIG. 2 is a top view of an embodiment of the present disclosure fully extended in anticipation of placement within the pelvic floor of a patient.

As shown in FIG. 2, apparatus 100 is a fan-like, compressible polyethylene or TPU bilayer 101 enveloping multiple wedged foam or sponge strips 105. The number of sponge strips 105 is preferably five as illustrated in FIG. 2, however this number may be increased or decreased during apparatus manufacturing depending on the optimal sizes of the encased sponge strips. Specifically, if each of the foam strips is broadened, the number of strips would decrease, while a reduction in the surface area of each foam strip may necessitate increasing the number of strips. In any event, it is most preferable that the retracted and condensed apparatus be able to be withdrawn from the approximately less than 2 cm incision (109 in FIG. 1) through the tubing portion 107 as it exits the abdominal cavity.

There are randomly spaced perforations 102 on the polyethylene bilayer 101 as shown in FIG. 2. The number of perforations on the entire surface of the apparatus is variable. However, the perforations 102 are preferably sufficiently numerous and sufficiently scattered over the surface of the bilayer 101 as to cover the entirety of the bilayer in a manner such as that shown in FIG. 2, that is to say, such that the bilayer does not have large regions of its surface lacking any perforations 102. The shape and size of each perforation is also variable. In a preferred embodiment, each perforation is less than 0.3 cm. Optionally, there are perforations 104 in foam strips 105. These are distinct from the previously mentioned pores that are an inherent feature of conventional reticulated foams. As with perforations 102, perforations 104 are preferably sufficiently numerous and sufficiently scattered over the foam strips 105 as to cover the entirety of their surfaces shown in FIG. 2, in a manner such as that shown in FIG. 2, that is to say, such that the surfaces of foam strips 105 do not have large regions lacking any perforations 104. The perforations 104 in a foam strip 105 extend from one side of the foam to the other, i.e. they go through the foam in the thickness direction (into the page, in FIG. 2). In contrast, while the perforations 102 of each polyurethane or polyetheylene bilayer also extend through each individual polyurethane or polyethylene layer, they do not extend through to the second layer of the bilayer. Thus, the perforations 102 in one layer of the bilayer are offset (in the direction(s) of the length and/or the width of the page, in FIG. 2) from the perforations 102 in the other layer of the bilayer, which permits formation of an airtight or near airtight seal between the two layers of the bilayer. This feature facilitates fluid exchange through the foam strip 105 when negative pressure is applied.

Cut lines 103 are used to accommodate use of the apparatuses in patients with smaller bowels. As previously stated, the apparatus may be cut to reduce the overall radius (size) of the non-tube portion to accommodate smaller abdominal cavities. The recommended process for reducing the radius involves making a semicircular cut through the broader foam (non-wedge) regions of all of the strips in the apparatus 100, pulling out the excess foam from each of the strips and allowing the polyurethane bilayer to self-seal. It is important that the bilayer be allowed to seal so that no foam comes into direct contact with any tissue, as this could lead to inadvertent attachment of foam to tissue, which would make later removal of the entire apparatus 100 difficult and painful for the patient.

The plurality of wedge-shaped foam or sponge strip portions joins seamlessly to a connecting sponge region 106. Alternatively, the plurality of wedge-shaped foam strips may become narrowed to a smaller width as they taper seamlessly to a connecting sponge region 106 (not shown). The entire plurality of sponge strips enveloped in a bilayer portion (the non-tubing portion) is further sealed by any conventional means to a tube-like extension of silicone 107 which extends across the abdominal cavity to the exterior thereof and is connected to a vacuum source. Sponge strips 105 are parallel (in terms of a polar coordinate system such as would be understood to apply to the partial-circular fan shape of the apparatus 100 as seen in FIG. 2) and extend from near the radially outer end of the fan (i.e., near the circumference if the fan were a circle) to element 106, which lies at/near the radially inward end.

Also, as illustrated in FIG. 2, there are parallel indentations or creases 108, one (as shown in FIG. 2, or more) disposed between each pair of adjacent foam strips 105 (parallel to the pair), which facilitates the pleating or folding (fan-like) of the apparatus during retraction from the abdomen. The number, radius (i.e., extent, length) and depth of these pleats 108 is variable and may be optimized depending on the number of foam strips 105 present and the dimensions of the foam strips. (Again, the use of the term "parallel"

refers here to the above-mentioned polar coordinate system, not a Cartesian coordinate system.)

Figure 3A:
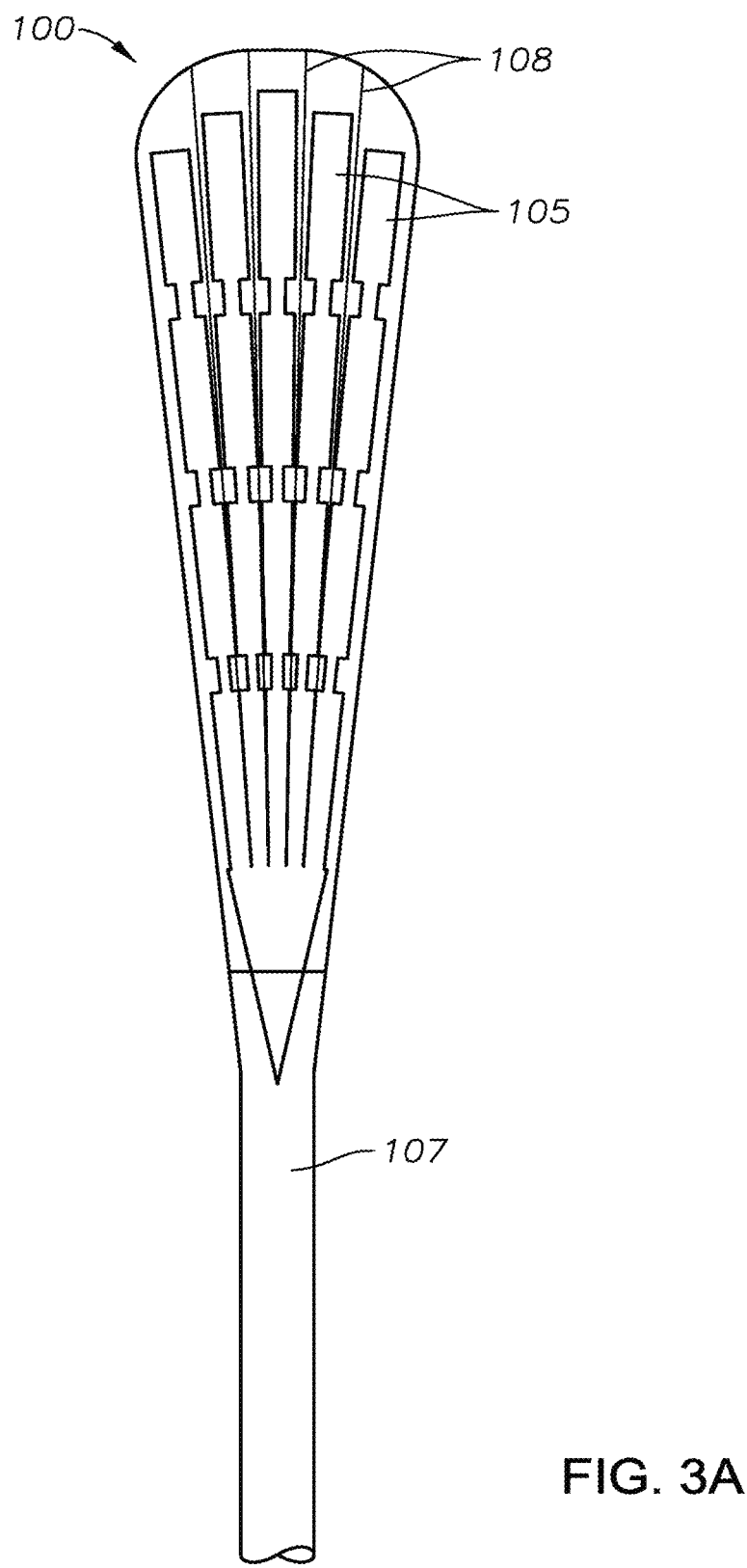
FIG. 3A is a top view of an embodiment of the present disclosure retracted through an approximately 2 cm incision (not shown) and removed from the pelvic floor of a patient (not shown)

FIG. 3A depicts the apparatus of FIG. 2 in its retracted or contracted state. As shown, indentations 108 facilitate the fan-like "folding" of the apparatus to reduce the overall dimensions of the apparatus and permit retraction of the apparatus from the approximately 2 cm incision to the exterior of the abdomen. As the abdominal cavity is closed after placement of the apparatus, this retract-ability feature obviates the need for additional surgery to remove the apparatus following post-operative recovery.

Figure 3B:
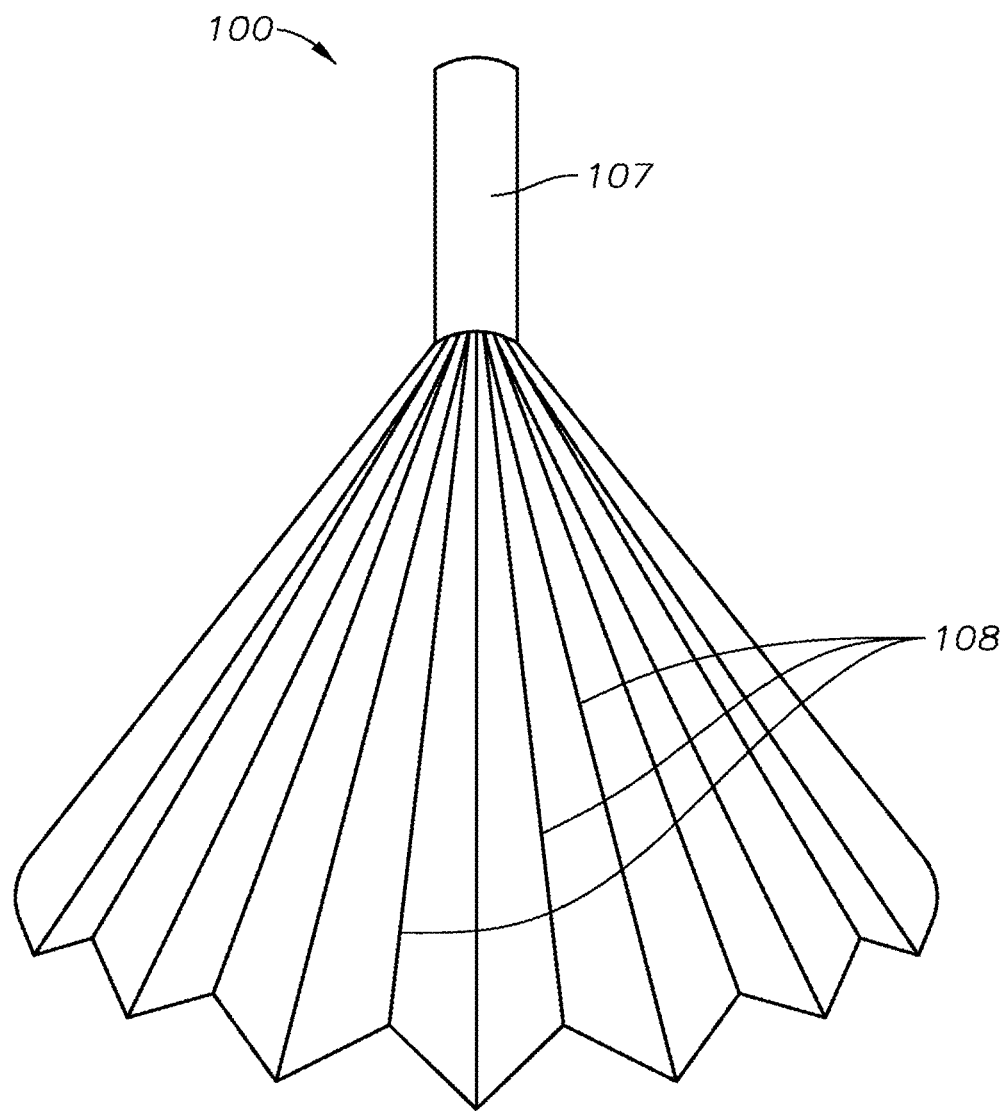
FIG. 3B is a perspective sectional view of the creased aspects of present disclosure which assist in retraction and removal.

FIG. 3B is a hypothetical perspective sectional view of apparatus 100 viewed from the radially outward edge thereof. FIG. 3B shows the creased aspect of apparatus 100, which assists in retraction and removal of the apparatus from the abdomen. Indentions 108 in the non-tube-like portion assist in the folding and removing of the apparatus by simply tugging on the tube-like portion 107 which is dangling from the 2 cm excision. As previously noted, the presence of parallel pleats or indentations on either side of a foam strip facilitates retraction by making it easier for the apparatus 100 to "fold up". This is similar to the functioning of a foldable fan so that a non-surgeon may remove it from the now closed abdomen of a patient when normal bowel function has returned (approximately 48 to 72 hours after abdominal closure).

Figure 4:
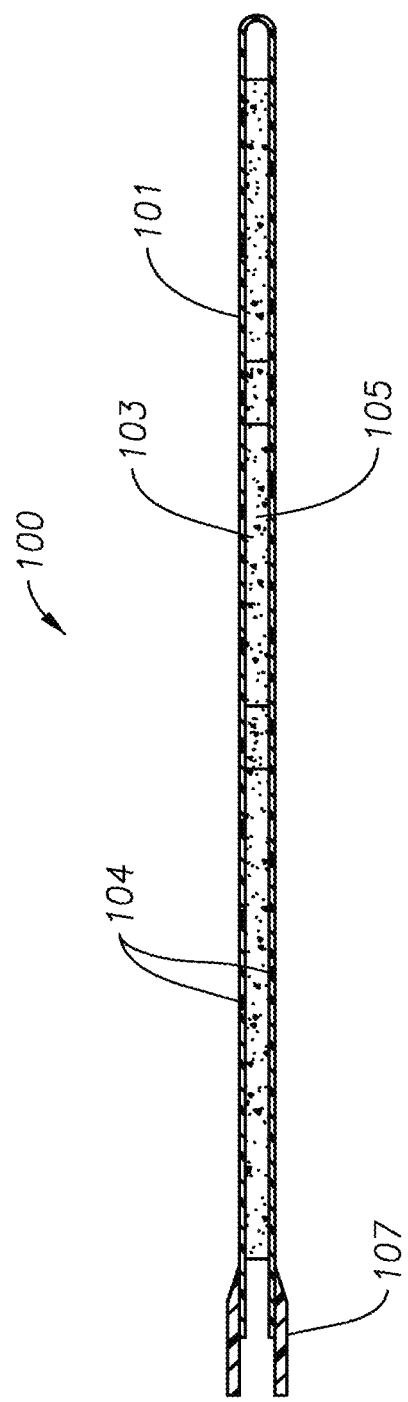
FIG. 4 is a cross sectional side view of an embodiment illustrating the various components and offset perforation in the polyurethane bilayer.

FIG. 4 is an exploded cross sectional side view of an embodiment illustrating the offset perforations 104 in the polyurethane or polyethylene bilayer 101; the heat sealing of the bilayer at the exterior radial end of the apparatus (described further in FIG. 5) and the fusion of the silicone tubing 107 to the bilayer. As discussed, the bilayer 101 encompasses numerous foam or sponge strips 105 disposed within it. As also discussed, optionally, depending on patient's bowel size, the radius (size) of the entire apparatus 100 may be reduced by cutting along cut line 103 (see above, FIG. 2). As seen in FIG. 4, the perforations 104 in bilayer 101, one in the upper layer and one in the lower layer (i.e., "upper" and "lower" as shown in FIG. 4), are offset from each other in radial direction of the apparatus 100 (which is the left-right direction in FIG. 4, and the top-bottom direction in FIG. 2).

Figure 6:
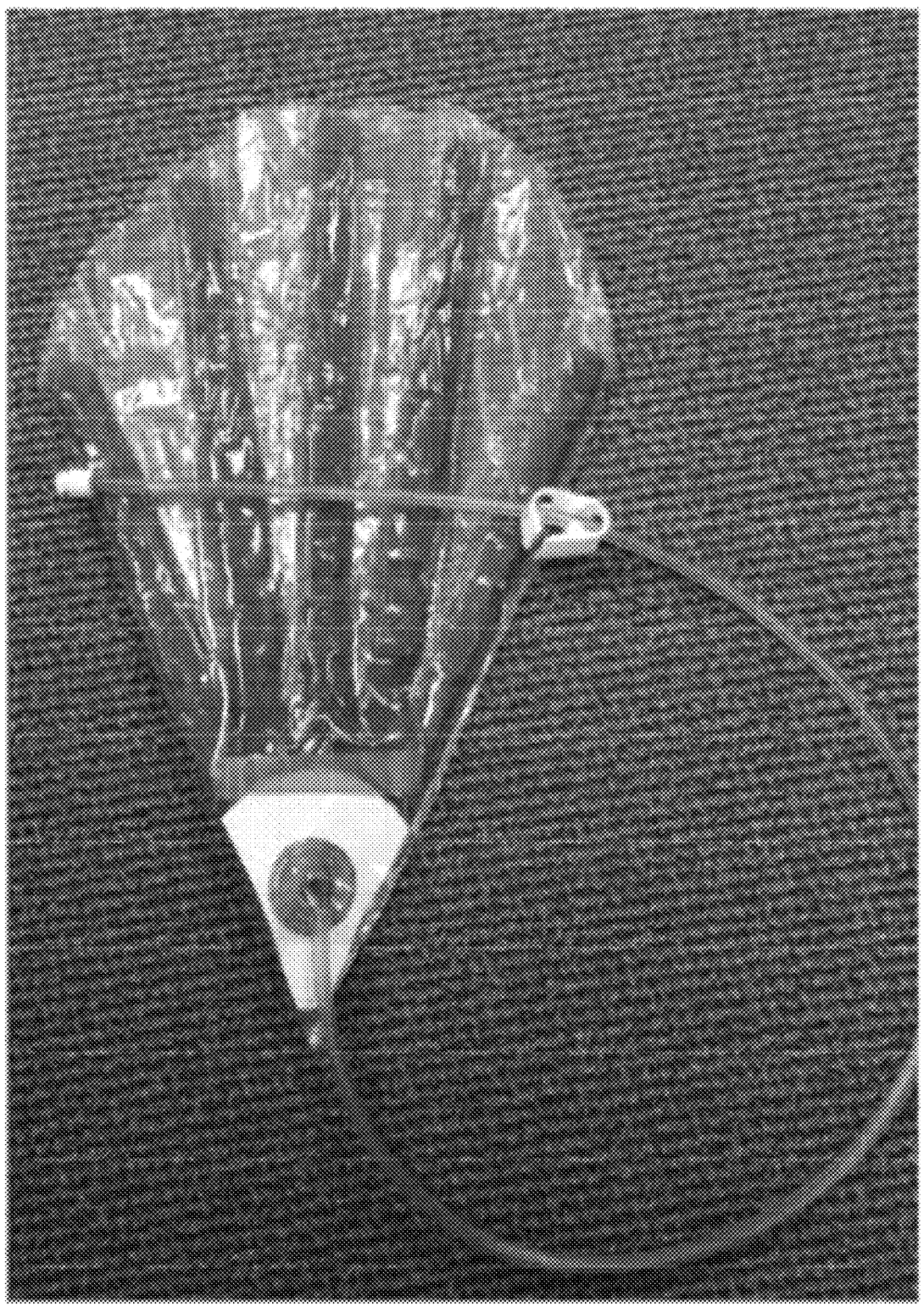
FIG. 6 is a black and white photograph of a top view of an embodiment of the present disclosure similar to FIG. 2 wherein the apparatus is fully extended with tubing which may be connected to a negative pressure means after placement within a patient.

The tubing (or tube-like portion) 107 is preferably silicone and biocompatible but may be made of any material known in the art. As shown in FIG. 4, the tubing 107 is pre-fused to both layers of the sealed (not shown) polyurethane bilayer. It is approximately 24 inches long to facilitate extending across the abdominal cavity to exit from an approximately 2 cm incision (109 in FIG. 1). This tubing portion 107 is preferably non detachable from the rest of apparatus 100 as this protects against leakage of fluid at the connection point between the silicone tubing and the polyethylene bilayer. Alternatively, it is contemplated that the tubing portion 107 be detachable so as to maximize portability and adaptability as shown in FIG. 6.

Figure 5:
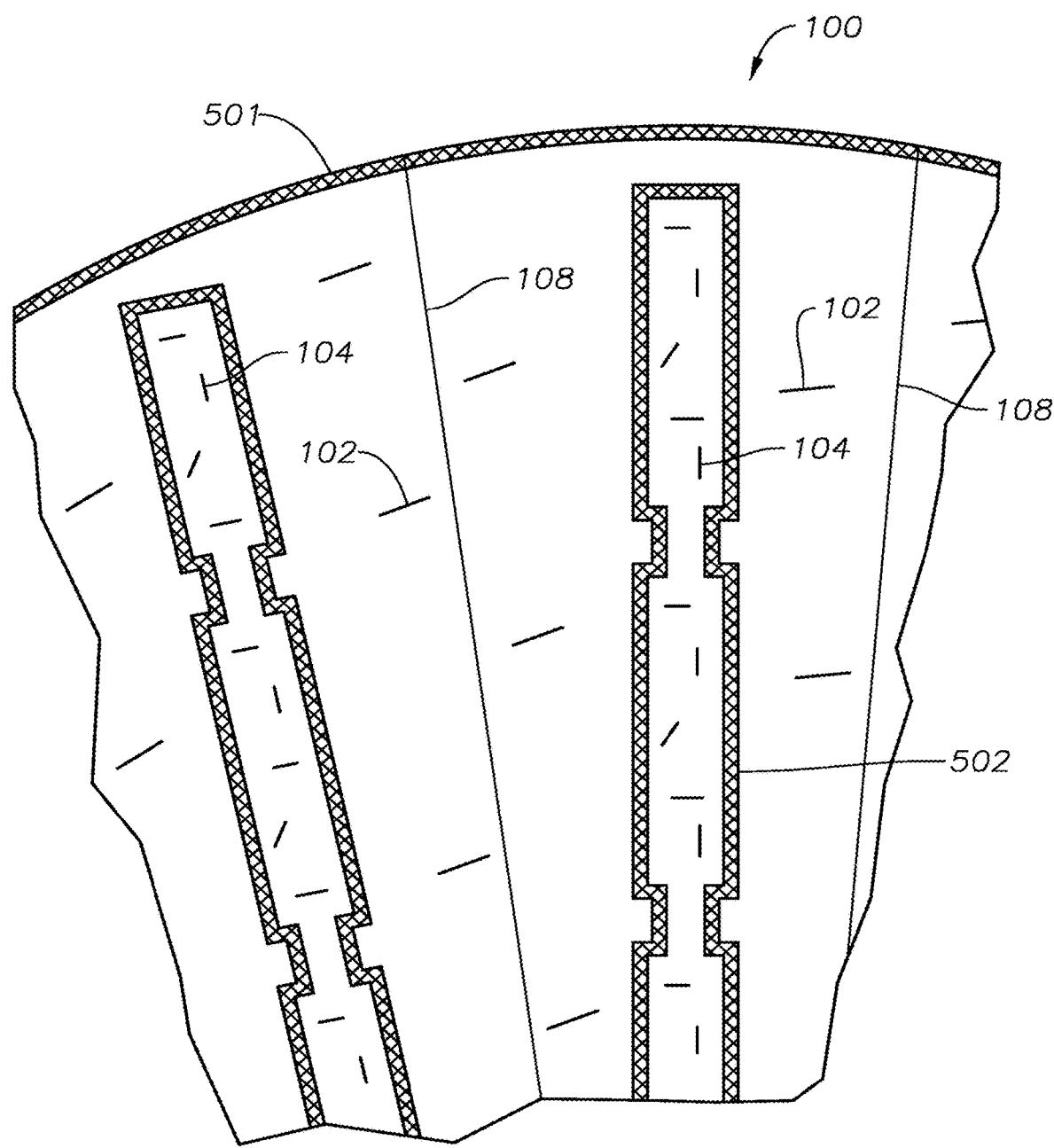
FIG. 5 is a partial perspective view of the components embodying some aspects of the present disclosure.

Another aspect of the present disclosure as illustrated in FIG. 5, is the use of heat sealing to join together the two layers of the bilayer 101. The sheets or layers of the bilayer 101 are heat sealed along their entire (common) perimeter 501 to ensure structural integrity especially during the stress of compression and removal of the apparatus from the abdominal cavity. This sealing also provides the airtight seal mentioned above, that facilitates removal of fluid through the perforations 104 in the wedge foam strips 105 by the vacuum pressure. (While FIG. 5 shows only a portion of heat-sealed perimeter 501 of apparatus 101, it is understood and also seen in FIG. 2 that the entire perimeter 501 is heat-sealed. Note while FIG. 2 shows perimeter 501 it is not labeled with a reference numeral.) Heat sealing is also used along the periphery 512 of each wedge-shaped foam strip 105, and the seal is contoured to fit the shape of the foam piece. This serves the dual purpose of sealing each of the layers of polyurethane around each foam strip as well as facilitating removal of the foam if a semicircular cut is required to reduce the radius/size of the entire apparatus 100. After a cut is made, the foam core may be left "floating" in the polyethylene bilayer without the seal. This would increase the likelihood of the foam coming into contact with patient tissues which increases likelihood of infection and pain during apparatus removal. Optionally, there may be additional heat sealing to improve overall apparatus integrity.

The narrowing of the foam strips at regular intervals (to form the wedges along each strip) may reduce the weight and overall dimensions of the foam strips. This narrowing is seen in FIG. 5 (two narrowed wedge regions at different radial locations in each strip 105) and in FIG. 2 (four narrowed wedge regions at different radial locations in each of the three central strips 105, and three narrowed wedge regions at different radial locations in each of the rightmost and leftmost strips 105,) However, it is also contemplated that no wedge-like regions within the reticulated foam strips are present to facilitate ease of manufacturing.

In prototyping an embodiment of the present disclosure, various materials were utilized. The attachment means for the tubing 107 that delivers negative pressure may be integrated into the apparatus of the present disclosure as in FIG. 2. Alternatively, as illustrated by the black and white photograph in FIG. 6, the tubing may be securely attached separately by any means known in the art. It is preferred that the tubing be connected to a stand-alone negative pressure device with a pressure regulator (not shown) after placement within a patient. However, any means for providing negative pressure with or without a means to regulate the pressure (e.g. a vacuum line) may be used. In FIG. 6, the tubing was silicone rubber tubing with a 0.126" wall thickness but any dimension of tubing of any length, width, and diameter is contemplated by this disclosure.

Figure 7:
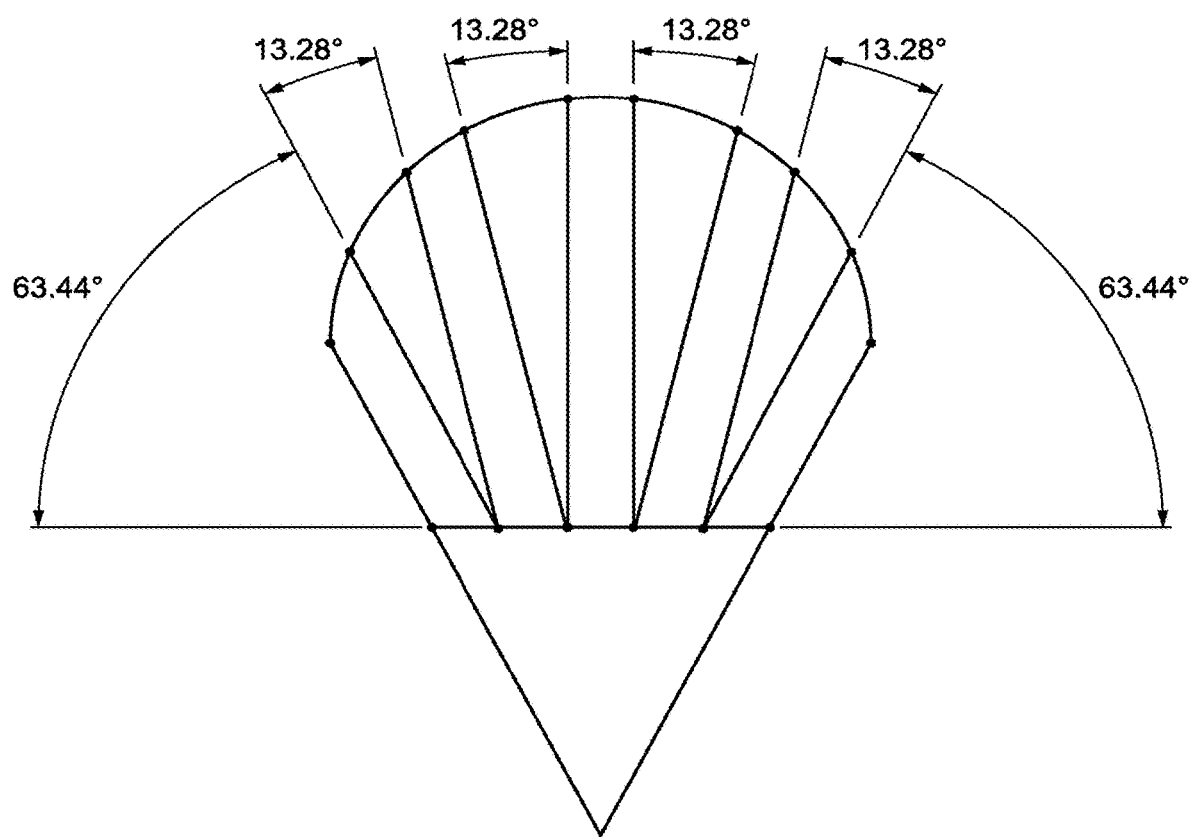
FIG. 7 is a top view of an embodiment of the present disclosure similar to FIG. 2 which were used to determine potential diameter dimensions of a prototype apparatus.

FIG. 7 is a top view of an embodiment of the present disclosure similar to FIG. 2 which were used to determine potential diameter dimensions of a prototype apparatus.

Figure 8:
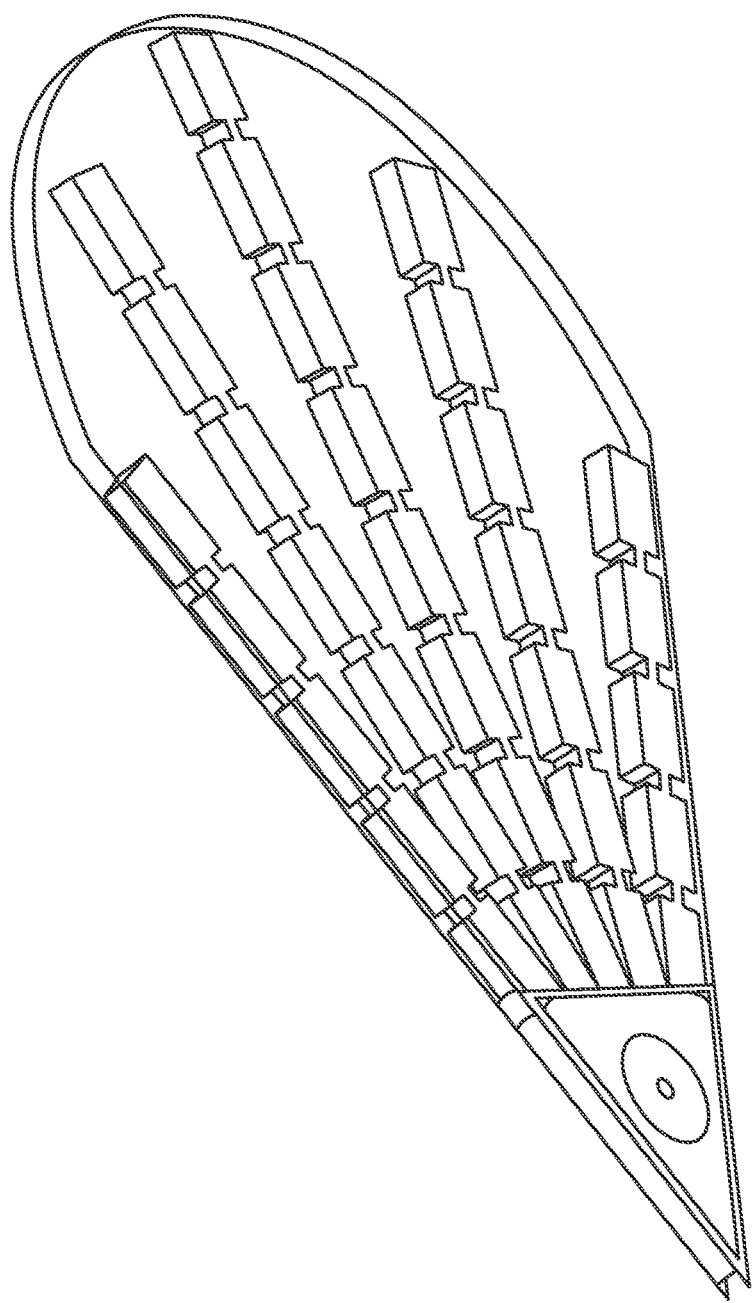
FIG. 8 is a side perspective view of an embodiment of the present disclosure similar to FIG. 7.

FIG. 8 is a side perspective view of an embodiment of the present disclosure similar to FIG. 7. In this embodiment, two sheets of TPU film from McMaster-Carr (Douglasville, GA) that was 0.015" thick was used to create a bilayer around open cell foam of ¼" thickness. In yet another embodiment, two sheets of 0.015" thick TPU film from McMaster-Carr was used to create a bilayer around open cell foam of ½" thickness (not shown).

Figure 9:
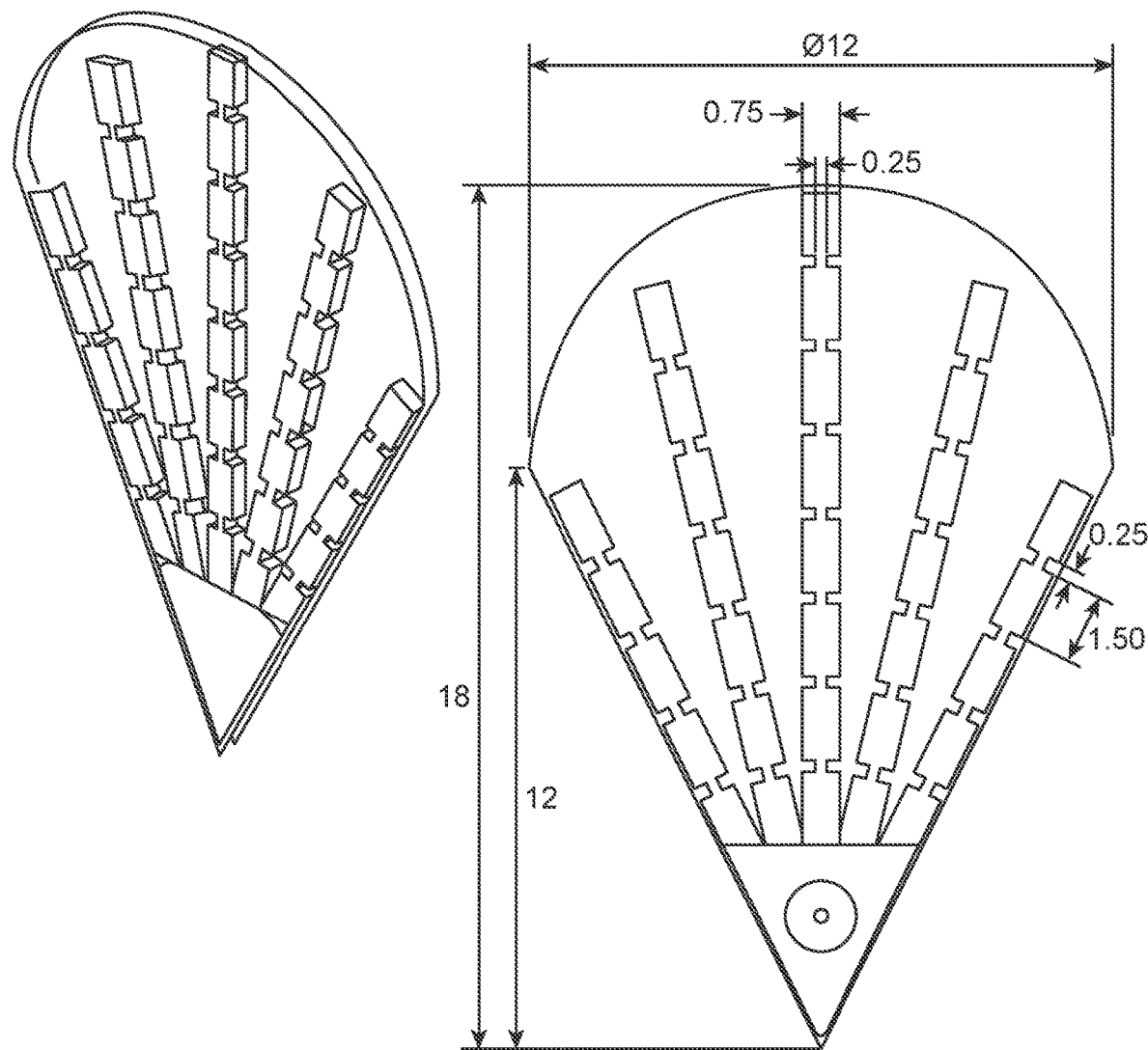
FIG. 9 is a composite of two perspective views of an embodiment of the present disclosure which were used to determine dimensions of a prototype apparatus.

FIG. 9 is a composite of two perspective views of an embodiment of the present disclosure which were used to determine dimensions of a prototype apparatus.

In addition, the exact compositions of the bilayer may be modified depending on the application, permeability and desirable flexibility. Additional enhancements to the foam and/or polyethylene/polyurethane or any of the components may be desirable and are contemplated. For example, the foam may incorporate conventionally known radiopaque additives. Thus, if any portion containing foam is left behind in a patient during the retraction process, use of a radiopaque foam can identify this upon x-raying the patient. This reduces patient complications that may arise due to such errors during surgery. Optionally, other luminescent or opaque materials embedded into one or all components of the dressing or other materials may be used to enhance visibility.

The apex (radially inward end) of each foam strip is integrated into a connecting sponge portion as shown in FIG. 2. Once the apparatus is placed in the abdominal cavity so that it supports the bowels, any conventional means to provide negative pressure such as a vacuum pump can be attached to the tubing portion 107 of the apparatus. The connector (not shown) between the vacuum pump tubing and the tubing portion 107 of the apparatus may be a Scienceware® Quick Connector from Bel-Arts Product. The specific components are two barbed polyethylene connectors that assemble tightly together with a male-female center taper. These connectors are specifically designed to be used in connecting and disconnecting vacuum lines and other tubing assemblies which are subject to great variations in pressure.

The pump can be set to deliver continuous or intermittent pressures, with levels of pressure depending on the device used, varying between—125 and—75 mmHg depending on the material used in the foam strips and patient tolerance. Pressure can be applied constantly or intermittently. As with standard negative pressure systems, continuous negative pressure (−125 mmHg) is recommended while pressures below-125 mmHg are not recommended. Pressure can be applied with a conventional medical grade vacuum pump or in emergency situations, any source of vacuum such as a portable hand-held suction pump.

This effects a pulling together of the tissue/wound edges and draining of excess fluid. Furthermore, "micro-massage effects" (also known as "microstrain" effect) may enable cell growth and stimulation of new tissue formation.

The present disclosure may also be used to decrease other post-operative complications such as infection and hematoma by removing blood and fluid in the post-operative abdominal cavity.

In light of the principles and example embodiments described and illustrated herein, it will be recognized that the example embodiments can be modified in arrangement and detail without departing from such principles. Also, the foregoing discussion has focused on particular embodiments, but other configurations are also contemplated. In particular, even though expressions such as "in one embodiment," "in another embodiment," or the like are used herein, these phrases are meant to generally reference embodiment possibilities, and are not intended to limit the invention to particular embodiment configurations. As used herein, these terms may reference the same or different embodiments that are combinable into other embodiments. As a rule, any embodiment referenced herein is freely combinable with any one or more of the other embodiments referenced herein, and any number of features of different embodiments are combinable with one another, unless indicated otherwise.

Similarly, although example processes have been described with regard to particular operations performed in a particular sequence, numerous modifications could be applied to those processes to derive numerous alternative embodiments of the present invention. For example, alternative embodiments may include processes that use fewer than all of the disclosed operations, processes that use additional operations, and processes in which the individual operations disclosed herein are combined, subdivided, rearranged, or otherwise altered.

This disclosure may include descriptions of various benefits and advantages that may be provided by various embodiments. One, some, all, or different benefits or advantages may be provided by different embodiments.

In view of the wide variety of useful permutations that may be readily derived from the example embodiments described herein, this detailed description is intended to be illustrative only, and should not be taken as limiting the scope of the invention. What is claimed as the invention, therefore, are all implementations that come within the scope of the following claims, and all equivalents to such implementations.

What is claimed is:

1. A method for preventing the onset and progression of Postoperative Ileus (POI), comprising: placing a device, comprising a plurality of foam strips enveloped in a bilayer and a connecting tube in fluid communication with the bilayer, so as to envelop the bowels; applying negative vacuum pressure therapy to the plurality of strips, thereby drawing out fluid from the bowel tissue and preventing the onset or progression of POI; collapsing the plurality of foam strips enveloped in the bilayer; and removing the plurality of foam strips enveloped in the bilayer by retraction from an internal patient cavity of the entire device in one piece through a surgical incision of diameter of less than 2 cm in a patient.

2. A method for treating a tissue region within a subject, comprising:
   positioning a device comprising one or more layers encompassing one or more pliable members in a deployed configuration upon the tissue region to be treated in an internal cavity of the subject;
   tensioning a connecting tube extending from and in fluid communication with the one or more layers at a radial end of the one or more layers such that the one or more layers collapse into a retracted configuration relative to the connecting tube; and
   withdrawing the one or more layers in the retracted configuration from the tissue region such that the entirety of the device including the connecting tube is withdrawn from the tissue region in one piece;
   wherein the connecting tube was placed in fluid communication with the one or more layers in a pre-manufactured configuration prior to positioning upon the tissue region.

3. The method of claim 2 wherein positioning the one or more layers further comprises actuating a negative pressure within the one or more pliable members such that a fluid from the tissue region is drawn into the one or more pliable members thereby preventing the onset or progression of Post-Operative Ileus.

4. The method of claim 3 further comprising removing the fluid through the connecting tube and from the subject.

5. The method of claim 3 wherein actuating the negative pressure further comprises drawing the fluid into the one or more pliable members through a plurality of openings distributed throughout the one or more layers.

6. The method of claim 2 wherein positioning the one or more layers further comprises leaving the one or more layers within the subject for a period of time prior to tensioning the connecting tube.

7. The method of claim 2 wherein positioning the one or more layers further comprises treating the tissue region via the one or more pliable members to prevent an onset or progression of Postoperative Ileus (POI), by drawing out fluid from the tissue region.

8. The method of claim 2 wherein positioning the one or more layers further comprises positioning the connecting tube through an incision within the subject such that the connecting tube extends external to the subject.

9. The method of claim 8 wherein withdrawing the one or more layers further comprises removing the one or more layers in the retracted configuration through the incision.

10. The method of claim 8 wherein the incision is less than 2 cm in size.

11. The method of claim 2 wherein positioning the one or more layers comprises inserting the one or more pliable members through an incision and upon the tissue region to be treated.

12. A method for preventing an onset or progression of Postoperative Ileus (POI within a subject, comprising:
- positioning a device comprising one or more layers encompassing one or more pliable members in a deployed configuration upon the tissue region to be treated within the subject;
- actuating a negative pressure within the one or more pliable members such that a fluid from the tissue region is drawn into the one or more pliable members, thereby preventing the onset or progression of POI;
- tensioning a connecting tube extending from and in fluid communication with the one or more layers at a radial end of the one or more layers such that the one or more layers collapse into a retracted configuration relative to the connecting tube; and
- withdrawing the one or more layers in the retracted configuration from the tissue region through a surgical incision of diameter of less than 2 cm in the subject, such that the entirety of the device including the connecting tube is withdrawn from the tissue region in one piece;
- wherein the connecting tube was placed in fluid communication with the one or more layers in a pre-manufactured configuration prior to positioning upon the tissue region.

13. The method of claim 12 wherein actuating the negative pressure further comprises removing the fluid through the connecting tube and from the subject.

14. The method of claim 12 wherein actuating the negative pressure further comprises drawing the fluid into the one or more pliable members through a plurality of openings distributed throughout the one or more layers.

15. The method of claim 12 wherein positioning the one or more layers further comprises leaving the one or more layers within the subject for a period of time prior to tensioning the connecting tube.

16. The method of claim 12 wherein the one or more layers further comprises positioning the connecting tube through an incision within the subject such that the connecting tube extends external to the subject.

17. The method of claim 16 wherein withdrawing the one or more layers further comprises removing the one or more layers in the retracted configuration through the incision.

18. The method of claim 16 wherein the incision is less than 2 cm in size.

19. The method of claim 12 wherein positioning the one or more layers comprises inserting the one or more pliable members through an incision and upon the tissue region to be treated.

* * * * *